United States Patent
Lee et al.

(10) Patent No.: US 9,335,310 B2
(45) Date of Patent: May 10, 2016

(54) METHOD FOR DETECTING AND ANALYZING MATERIALS CONTRIBUTING TO ODORS FROM AIR CONDITIONER

(71) Applicant: Hyundai Motor Company, Seoul (KR)

(72) Inventors: Tae Hee Lee, Gyeonggi-do (KR); Ji Wan Kim, Gyeonggi-do (KR)

(73) Assignee: Hyundai Motor Company, Seoul (KR)

( * ) Notice: Subject to any disclaimer, the term of this patent is extended or adjusted under 35 U.S.C. 154(b) by 326 days.

(21) Appl. No.: 13/874,745

(22) Filed: May 1, 2013

(65) Prior Publication Data

US 2014/0137636 A1 May 22, 2014

(30) Foreign Application Priority Data

Nov. 16, 2012 (KR) .......................... 10-2012-0130534

(51) Int. Cl.
| | | |
|---|---|---|
| *G01N 33/18* | (2006.01) | |
| *G01N 33/00* | (2006.01) | |
| *B60H 1/00* | (2006.01) | |
| *B60H 3/00* | (2006.01) | |

(52) U.S. Cl.
CPC ........ *G01N 33/0004* (2013.01); *B60H 1/00978* (2013.01); *B60H 3/0085* (2013.01)

(58) Field of Classification Search
CPC ............. G01N 33/0004; B60H 3/0085; B60H 1/00978
USPC ........................................ 73/23.34
See application file for complete search history.

(56) References Cited

U.S. PATENT DOCUMENTS

| | | | | |
|---|---|---|---|---|
| 3,815,405 | A | * | 6/1974 | Dravnieks ................. 73/23.34 |
| 3,902,851 | A | * | 9/1975 | Dravnieks ................. 73/23.34 |
| 6,834,530 | B2 | * | 12/2004 | Kita et al. ................. 73/23.34 |
| 8,852,946 | B2 | * | 10/2014 | Lee et al. ................... 436/9 |
| 2005/0191213 | A1 | * | 9/2005 | Casillas et al. ............. 422/99 |
| 2006/0130663 | A1 | * | 6/2006 | Joshi et al. ................. 96/224 |
| 2009/0320559 | A1 | * | 12/2009 | Lemieuvre et al. ......... 73/23.34 |

FOREIGN PATENT DOCUMENTS

| | | | |
|---|---|---|---|
| JP | 2-13819 | * | 1/1990 |
| JP | 2000171373 | A | 6/2000 |
| JP | 2001033362 | A | 2/2001 |
| JP | 2002174569 | A | 6/2002 |
| KR | 10-2004-0051143 | | 6/2004 |
| KR | 10-2005-0102347 | | 10/2005 |
| KR | 10-2009-0050422 | | 5/2009 |
| WO | 2009157187 | A1 | 12/2009 |

OTHER PUBLICATIONS

Kyung, H.k. et al., "Evaluation of Malodor for Automobile Air Conditioner Evaporator by Using Laboratory-Scale Test Cooling Bench", Journal of Chromatography A, vol. 1204, 2008, pp. 72-80.*

(Continued)

*Primary Examiner* — Daniel S Larkin
(74) *Attorney, Agent, or Firm* — Mintz Levin Cohn Ferris Glovsky and Popeo, P.C.; Peter F. Corless

(57) ABSTRACT

Disclosed herein is a method for detecting and analyzing materials contributing to a detected odor from an air conditioner. The method includes analyzing the detected odor using a sensory evaluation of the detected odor. A first gas sample is then collected and instrumental analysis is performed to determine a plurality of contributing materials of the detected odor.

3 Claims, 3 Drawing Sheets

(56) References Cited

OTHER PUBLICATIONS

Uchiyama et al., "Analysis for Absorbed Odor from Car Air Conditioner Evaporator", Denso Corporation and Toyota Central R&D Labs, Inc.

Kim, Kyung-Hwan, "A study on identification of odor active compounds emitted from an automobile air-conditioner evaporator", Dept. of Environ. Sci. Graduate School, Kangwon National University, 49 pages.

\* cited by examiner

CARBONYL GROUP 2,4-DINITROPHENYLHYDRAZINE STABLE COLOR WATER
(ALDEHYDES AND KETONES) (DNHP) HYDRAZONE DERIVATIVE

METHOD FOR DETECTING AND ANALYZING MATERIALS CONTRIBUTING TO ODORS FROM AIR CONDITIONER

CROSS-REFERENCE TO RELATED APPLICATIONS

This application claims priority under 35 U.S.C. §119 to Korean Patent Application No. 10-2012-0130534, filed on Nov. 16, 2012 in the Korean Intellectual Property Office, the disclosure of which is incorporated herein by reference in its entirety.

BACKGROUND (a) Technical Field

The present invention relates to a method of detecting and analyzing materials contributing to a detected odor from an air conditioner.

(b) Background Art

Clean air is an essential element for maintaining human health and well-being. Two important factors are generally associated with unsatisfactory indoor air quality in an airtight building including: the building itself producing a substantial amount of air pollutants that need to be removed or diluted; and odor generated as a result of human activities.

An air-cooling system lowers indoor temperature and optimizes indoor environment through air conditioning which changes air temperature, humidity, flow and cleanliness to more favorable conditions. Increasingly, air-cooling systems are being used to improve the standard of living. Although air-cooling systems have been improved functionally, over time, there remain problems to be solved in terms of indoor air quality. In the past, the function of lowering indoor temperature was viewed as one of the most fundamental and important functions of the air-cooling system. However, currently, health-related aspects such, as indoor air quality and odor are also regarded as important functions of air-cooling systems. In particular, complaints regarding indoor air quality include offensive odors, such as urine odor, foul odor, foot odor, and the like. To solve the odor problem, it may be necessary to analyze and detect the odor causing substances. However, a method for investigating materials causing odors from an air conditioner including evaluation of the odor, collection of gas, analysis of components, determining the substance causing the odor.

SUMMARY

The present invention provides a method for identifying and analyzing substances causing detected odors emitted from an air conditioner including analysis of the detected odor, collection of gas, analysis of components, and determining the contributing materials.

In one aspect, the present invention provides a method for analyzing materials causing odors emitted from an air conditioner, including the step of: analyzing a sensory evaluation of the odor; collecting a gas sample for instrumental analysis; analyzing the gas sample for instrumental analysis; and determining the materials contributing to the detected odor.

In another embodiment, the method for analyzing materials causing odors emitted from an air conditioner further includes enhancement of the odor intensity by one level.

In yet another embodiment, the method for analyzing materials causing odors emitted from an air conditioner further includes analysis of an odor pattern.

Other features and aspects of the present invention will be apparent from the following detailed description, accompanying drawings and claims.

BRIEF DESCRIPTION OF THE DRAWING

The above and other objects, features and advantages of the present invention will now be described in detail with reference to exemplary embodiments thereof illustrated in the accompanying drawing which is given hereinbelow by way of illustration only, and thus are not limitative of the invention, and wherein.

DETAILED DESCRIPTION

Figure 1:
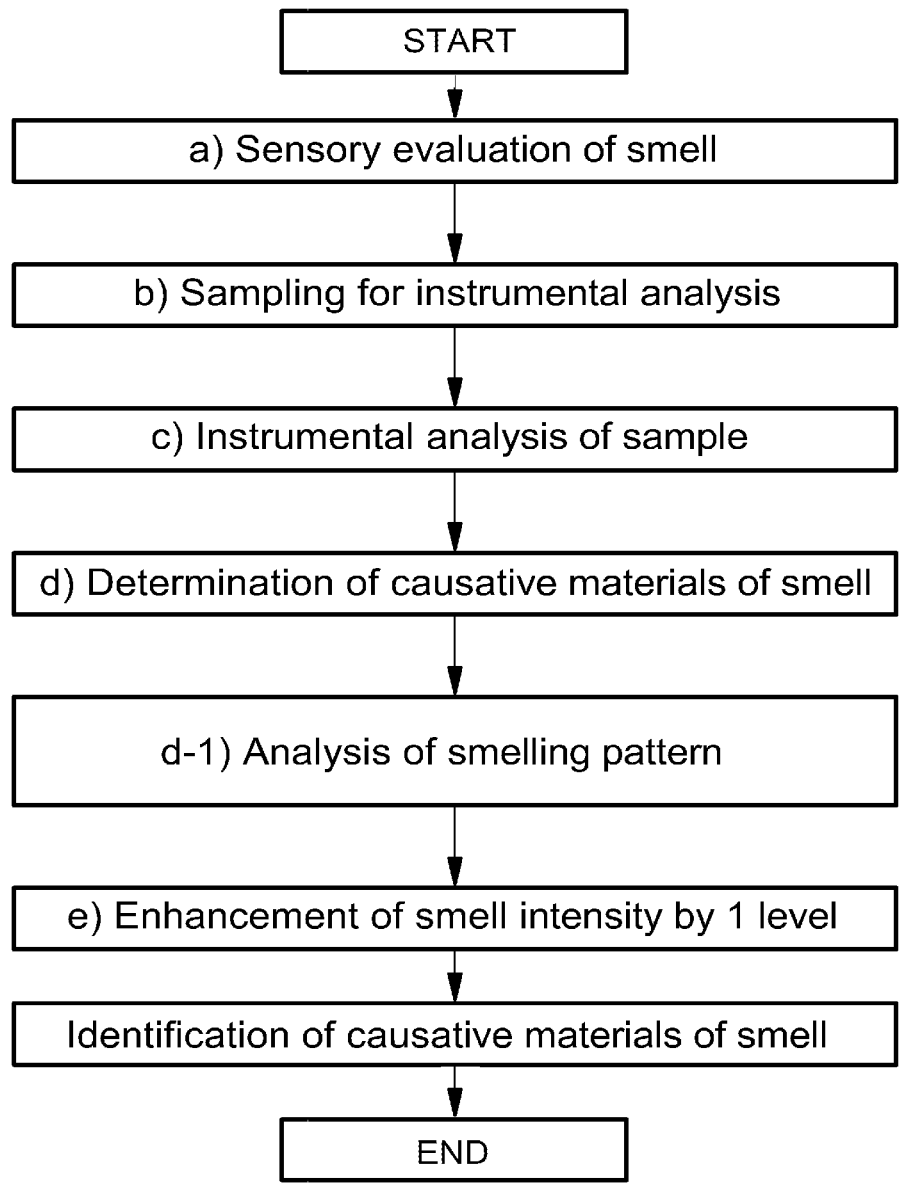
FIG. 1 is an exemplary flow chart describing a method for analyzing the contributing materials of an odor emitted from air conditioner according to an exemplary embodiment of the present invention.

It is understood that the term "vehicle" or "vehicular" or other similar term as used herein is inclusive of motor vehicles in general, such as passenger automobiles including sports utility vehicles (SUV), buses, trucks, various commercial vehicles, watercraft including a variety of boats and ships, aircraft, and the like, and includes hybrid vehicles, electric vehicles, combustion, plug-in hybrid electric vehicles, hydrogen-powered vehicles and other alternative fuel vehicles (e.g. fuels derived from resources other than petroleum).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Hereinafter, reference will now be made in detail to various exemplary embodiments of the present invention, examples of which are illustrated in the accompanying drawings and described below. While the invention will be described in conjunction with exemplary embodiments, it will be understood that the present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

In one embodiment, of the present invention the method for analyzing materials causing detected odors emitted from an air conditioner may include the steps described herein below.

a) Sensory Analysis of the Odor

The sensory analysis step may include hermetic sealing of automobile air conditioner exhausts, covering the exhaust system, and setting the air conditioner mode. More specifically, the analysis step may include a-1) hermetic sealing at least three of the automobile air conditioner exhausts, a-2) covering the remaining exhaust using a glass tube and a vinyl bag for sensory analysis and gas sampling, a-3) operating the air conditioner at level 2 under internal ventilation condition and a-4) analysis by a qualified panelist by smelling the gas collected in the glass tube and evaluation of the intensity and type of odor.

The qualified panelist may be selected as follows: five adult male and female panelists smell five pieces of test paper, three of which may be soaked with smelling reagents and the remaining two may be soaked with liquid paraffin and distilled water, respectively. The panelists correctly identifying the three smelling reagents and evaluating the intensity thereof as a level 3-4 may be considered qualified. The standard for the intensity of the odor is described in Table 1.

TABLE 1

| Odor intensity | Level of odor |
| --- | --- |
| 5 | Irritating and intense odor |
| 4 | Strong odor |
| 3 | Weak but easily perceived odor |
| 2 | Perceived but slight odor |
| 1 | Almost unperceived odor |
| 0 | No odor | b) Collecting a First Gas Sample for Instrumental Analysis

The air circulating in the air-conditioning system of the automobile may be collected. Specifically, the sampling step may include b-1) hermetic sealing of at least three automobile air conditioner exhausts, b-2) sealing the remaining exhaust using a glass tube and a vinyl bag, b-3) connecting the opening of a 10-L PE sample bag to the glass tube and b-4) operating the air conditioner at level 2 under internal ventilation condition followed by collecting a gas sample.

c) Instrumental Analysis of Sample

In the analysis step, the collected gas sample may be analyzed using the methods and instruments described below.

The methods for evaluation of 22 foul odor substances specified by the Korean Malodor Prevention Act and the volatile organic compounds (VOCs) expected to occur frequently are described in Table 2.

TABLE 2

| Components | Sampling | Pretreatment | Detector |
| --- | --- | --- | --- |
| Ammonia | Vinyl bag | Boric acid absorption | UV/VIS |
| Amines | | Sulfuric acid absorption | MSD |
| Sulfur compounds | | Cold trap | FPD |
| Aldehydes | | DNPH cartridge reaction followed by extraction with acetonitrile | HPLC |
| VOCs | | Cold trap | MSD |
| Short-chain fatty acids | | Alkaline absorption | MSD |

The instrumental analysts of the various gas samples may be conducted as described below.

1. Ammonia 5 mL of phenol-sodium nitrosylpentacyanoferrate(III) solution and 5 mL of sodium hypochlorite solution may be added to a sample solution to be analyzed. After reaction in a water bath of about 25-30° C. for about 1 hour, absorbance of indophenol produced from a reaction with ammonium ion may be measured to quantitatively detect ammonia (indophenol method). After the reaction solution turns blue, detection may be made at about 640 nm using a UV/vis detector (e.g., CARY-50, USA).

2. Trimethylamine 5 mL of 50% KOH may be added to a vial holding a sample solution to be analyzed. After shaking the sample solution for about 5 minutes using an SPME auto sampler (MH01-00B), trimethylamine eluted to the headspace of the vial may be adsorbed by a solid-phase microextraction (SPME) in about 15 minutes and then analyzed by gas chromatography (GC/MSD).

3. Sulfur Compounds

Sulfur compounds may be detected using a pump-type vacuum aspiration box (e.g., Model 1062, Youngwha Scientific) and a Tedlar bag (e.g., 5 L, 10 L, Japan). The Tedlar bag may be flushed with substantially pure nitrogen (e.g., 99.999%) at least 3 times before the detection and sampling is performed; and then a sample may be released at least once. The bag containing the sample may be stored and transported at room temperature (e.g., 15-25° C.) while avoiding direct sunlight and analysis may be performed within about 24 hours. Furthermore, the analysis may be performed by gas chromatography (e.g., CP3800, Varian, U.S.A) using a pulsed flame photometric detector (PFPD) capable of detecting sulfur compounds.

4. Aldehydes

Figure 3:
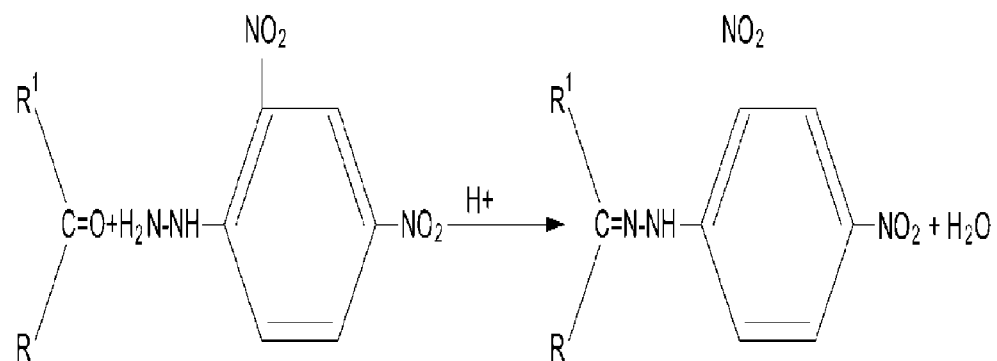
FIG. 3 illustrates a derivatization of carbonyl compounds.

As shown in FIG. 3, aldehydes may be detected by 2,4-dinitrophenylhydrazine (2,4-DNPH) derivatization whereby substantially stable DNPH derivatives may be produced from a reaction of carbonyl compounds (e.g., aldehyde and ketones) with 2,4-DNPH. Additionally, FIG. 3 illustrations an exemplary derivatization of carbonyl compounds by 2,4-DNPH. Through this reaction, the carbonyl compounds may be converted to substantially stable 2,4-DNPH hydrazone derivatives and water ($H_2O$) may be produced as a byproduct. Moreover, aldehydes may be sampled using a 2,4-DNPH cartridge with purified 2,4-DNPH coated on a polypropylene tube. An ozone scrubber filled with potassium iodide (KI) may be attached to the 2,4-DNPH cartridge to remove the ozone that may interfere with the detection of aldehydes.

After the detection is completed, the sample may be packaged individually in a container, the interior and exterior of which may be coated with aluminum and the container may be stored below about 4° C. until solvent extraction occurs. Extraction may be carried out at a substantially low speed (e.g., 1 mL/min) using about 2.5 mL of acetonitrile. The aldehydes may be analyzed by high performance liquid chromatography (HPLC) (e.g., Prostar325, Varian, U.S.A.).

5. Volatile Organic Compounds (VOCs)

Volatile organic compounds such as: styrene, toluene, xylene, methyl ethyl ketone (MEK), methyl isobutyl ketone (MIBK), butyl acetate and isobutyl alcohol, which are designated as offensive odor substances, may be measured using a Tenax-TA adsorption tube (e.g., Supelco, U.S.A) in which at least 200 mg of the Tenax-TA adsorbent is added to the tube. After the detection is completed, the sample may be stored below about 4° C. Furthermore, analysis may be performed by GC/MSMS (e.g., 3800GC/1200 L, Varian, U.S.A.).

6. Organic Acids 2.3 g of sodium chloride (NaCl) may be added to a vial containing a sample solution to be analyzed. After adding about 1 mL of 2% sulfuric acid ($H_2SO_4$), the sample may be sufficiently mixed. In addition, after shaking the vial at about 90° C. for about 20 minutes using an SPME auto sampler (e.g., MH01-00B), organic acids eluted to the headspace of the vial may be adsorbed by SPME in about 15 minutes and may then be analyzed by gas chromatography (GC/MSD).

The analysis results for the samples are given in Tables 3-6.

TABLE 3

| Components | Concentration (ppb) |
|---|---|
| Ammonia | 0.0 |
| Acetaldehyde | 25.1 |
| Propionaldehyde | 0.0 |
| Butyraldehyde | 0.0 |
| Isovaleraldehyde | 0.0 |
| Valeraldehyde | 4.8 |
| Hydrogen sulfide | 0.0 |
| Methyl mercaptan | 0.0 |
| Dimethyl sulfide | 0.0 |
| Dimethyl disulfide | 0.0 |
| Trimethylamine | 0.0 |
| Toluene | 57.7 |
| m,p-Xylene | 17.9 |
| o-Xylene | 8.6 |
| Styrene | 0.5 |
| Methyl ethyl ketone | 0.7 |
| Methyl isobutyl ketone | 4.0 |
| Butyl acetate | 10.9 |
| Propionic acid | 0.0 |
| n-Butyric acid | 0.0 |
| n-Valeric acid | 0.0 |
| Isovaleric acid | 0.0 |
| Isobutyl alcohol | 2.4 |

TABLE 4

| Components | Concentration (ppb) |
|---|---|
| 2-Heptanone, 7,7,7-trichloro- | 1.2 |
| Silane, methyl- | 1.2 |
| 1,4-Pentadiene | 0.5 |
| Hexane, 3,3,4,4-tetrafluoro- | 1.6 |
| Pentane, 2-methyl- | 0.8 |
| Propane, 1-chloro-2-methyl- | 0.6 |
| Oxetane, 2,3,4-trimethyl-, (2.alpha.,3.a) | 8.9 |
| 2-Propanol, 1-methoxy- | 2.9 |
| Sulfide, allyl methyl | 0.8 |
| Heptane | 0.5 |
| Methyl isobutyl ketone (MIBK), 4-methyl- | 1.3 |
| Toluene | 24.4 |
| Hexanal | 0.9 |
| Acetic acid, butyl ester | 5.7 |
| Heptane, 2,4-dimethyl- | 0.4 |
| Cyclotrisiloxane, hexamethyl- | 1.4 |
| Heptane, 2,4-dimethyl- | 0.8 |
| Butanoic acid, 2-methyl-, ethyl ester | 1.1 |
| 1-Methoxy-2-propyl acetate | 4.6 |

TABLE 5

| Components | Concentration (ppb) |
|---|---|
| Ethylbenzene | 2.6 |
| o-Xylene | 8.4 |
| Octane, 4-methyl- | 0.2 |
| Heptanal | 0.7 |
| o-Xylene | 4.1 |
| Ethanol, 2-butoxy- | 10.1 |
| Decane, 2,5,6-trimethyl- | 1.2 |
| Hexanoic acid, methyl ester | 0.6 |
| 2-Pentanol, 4,4-dimethyl- | 0.5 |
| n-Propylbenzene | 1.0 |

TABLE 5-continued

| Components | Concentration (ppb) |
|---|---|
| Benzene, 1,2,3-trimethyl- | 4.0 |
| Benzene, 1,2,3-trimethyl- | 1.6 |
| Propanoic acid, 3-ethoxy-, ethyl ester | 1.2 |
| Benzene, 1,3,5-trimethyl- | 4.0 |
| Decane, 2,5,6-trimethyl- | 1.3 |
| Benzene, 1-ethyl-2-methyl- | 1.9 |
| Pentanoic acid, 4-methyl-, ethyl ester | 1.3 |
| Octanal | 1.2 |
| Benzene, 1,2,3-trimethyl- | 9.0 |
| Cyclotetrasiloxane, octamethyl- | 1.0 |
| Decane | 3.0 |
| 2-Propyl-1-pentanol | 6.1 |
| Benzene, 1,2,3-trimethyl- | 3.5 |
| Decane, 2,6,7-trimethyl- | 1.6 |
| Cyclohexene, 1-methyl-5-(1-methylethenyl) | 2.3 |
| Decane, 2-cyclohexyl- | 0.9 |

TABLE 6

| Components | Concentration (ppb) |
|---|---|
| 2-Propyl-1-pentanol | 6.1 |
| Benzene, 1,2,3-trimethyl- | 3.5 |
| Decane, 2,6,7-trimethyl- | 1.6 |
| Cyclohexene, 1-methyl-5-(1-methylethenyl) | 2.3 |
| Decane, 2-cyclohexyl- | 0.9 |
| 2-(1-Hydroxyethyl)hydroxymethylbenzene | 1.4 |
| Decane, 2,6,7-trimethyl- | 3.6 |
| Hydroxylamine, O-decyl- | 1.3 |
| Benzene, 4-ethyl-1,2-dimethyl- | 1.1 |
| Nonanal | 5.6 |
| 2-Propenoic acid, tridecyl ester | 0.8 |
| Undecane | 4.5 |
| Decane, 2,4,6-trimethyl- | 1.4 |
| Benzene, 1,2,4,5-tetramethyl- | 1.3 |
| Benzene, 1,2,4,5-tetramethyl- | 2.1 |
| p-Trimethylsilyloxyphenyl-(trimethylsilyl) | 14.5 |
| 3-Hydroxymandelic acid, ethyl ester, di- | 0.1 |
| Cyclohexanol, 5-methyl-2-(1-methylethyl) | 0.8 |
| Decanal | 1.3 |
| Tridecane | 1.4 |
| 4-(Prop-2-enoyloxy)octane | 0.3 |
| Trisiloxane, 1,1,1,5,5,5-hexamethyl-3,3- | 0.4 |
| Trisiloxane, 1,1,1,5,5,5-hexamethyl-3,3- | 0.9 |
| Pentadecane | 1.1 |
| Decane | 1.5 |
| Silane, dimethyl(dimethyl 2-iso) | 36.3 |
| Hydroxylamine, O-decyl- | 0.2 |
| Tridecane | 1.7 |
| 3-Isopropoxy-1,1,1,7,7,7-hexamethyl-3,5, | 2.8 | d) Determination of Materials Contributing to the Detected Odor

The step of determining the materials contributing to the detected odor may include a primary determination of 22 representative offensive odor causing materials, the addition of VOCs, and the analysis of an odor pattern. Although many components may be detected as a result of gas analysis, not all of the detected results may be a cause of the detected odor. The present invention relates to a method for analyzing materials contributing substantially to the offensive odor emitted from the air conditioner based on analysis of the first gas sample.

Additionally, the 22 representative offensive odor causing materials are determined prior to analysis of the gas sample. Furthermore, by combining the 22 various representative substances, the odor may be reproduced by comparing the sensory analysis results.

Moreover, when the detected odor is not produced using the 22 representative substances, VOCs may be added to the sample. Specifically, a threshold value may be determined based on the combination of the 22 various representative substances and the similarity to the detected odor. Additionally, a table for odor may be constructed based on the sensory analysis of the odor and the addition of various components contributing to the similarity of the odor. In other words, the threshold value indicates how similar the reproduced odor and the detected odor are based on the sensory analysis results.

Moreover, the method according to the present invention may further include a step of analyzing the odor pattern, wherein intensity of the odor may be analyzed while the air conditioner is operating and while the air conditioner is not operating. For example, the quality and intensity of odor may change as the air conditioner is turned on or off. Accordingly, a second gas sample may be collected when the quality and intensity of odor changes according to the following criteria and components may be combined according to the odor pattern.

Pattern analysis step 1: [A/C off−indoor air]>0,

Pattern analysis step 2: [A/C off−A/C on]>0 or

Pattern analysis step 3: [(A/C off−indoor air) and (A/C off−A/C on)]>0

Figure 2:
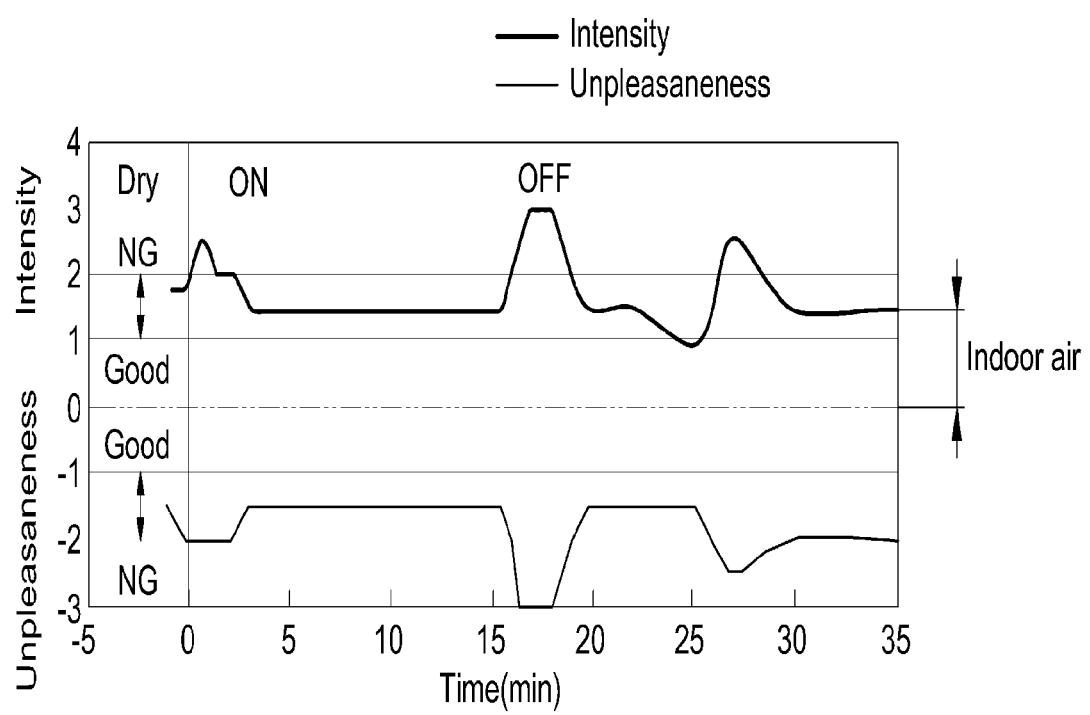
FIG. 2 is an exemplary odor pattern of an offensive odor emitted from an air conditioner obtained by determining contributing materials according to an exemplary embodiment of the present invention.

The above gas analysis equations may be obtained from the pattern shown in FIG. 2. Furthermore, since odor is not detected in the interior air or when the air conditioner is turned on, contributing materials of the offensive odor may be eliminated by comparing the analysis result for the gas collected when the air conditioner is turned off with that of the interior air or the gas collected when the air conditioner is turned on.

Referring to FIG. 2, as the air conditioner is turned on, water is condensed resulting in a cooling effect and an offensive odor may be detected. When blowing of air occurs while the air conditioner turned off, the surface of an evaporator core of the air conditioner may become dry due to air flow. As a result, the evaporator core surface may change from wet to dry state and the offensive odor may be detected.

The method according to the present invention may further include a step e) of enhancing odor intensity by 1 level. The offensive odor is an odor which is stronger than the interior air by 1 level or more. In general, no odor is detected in the interior air or when the air conditioner is turned on continuously. In other words, the odor intensity may be low and the concentration of the causative materials of odor may also be low as compared to the offensive odor. The offensive odor may be detected when the intensity is at least 1 level higher than level 2. Accordingly, the odor may be reproduced by increasing the concentration of the determined contributing materials by 1 level. Specifically, the odor intensity is based on a table of values obtained through experimentation as shown in Table 7 below.

TABLE 7

(unit: ppm)

Odor Intensity (odor intensity indication in 6 levels)

| Name | 1 | 2 | 2.5 | 3 | 3.5 | 4 | 5 |
|---|---|---|---|---|---|---|---|
| ammonia | 0.1 | 0.6 | 1 | 2 | 5 | $1 * 10$ | $4 * 10$ |
| methyl mercaptan | 0.0001 | 0.0007 | 0.002 | 0.004 | 0.01 | 0.03 | 0.2 |
| hydrogen sulfide | 0.0005 | 0.006 | 0.02 | 0.06 | 0.2 | 0.7 | 8 |
| dimethyl sulfide | 0.0001 | 0.002 | 0.01 | 0.05 | 0.2 | 0.5 | 2 |
| dimethyl disulfide | 0.0003 | 0.003 | 0.009 | 0.03 | 0.1 | 0.3 | 3 |
| trimethyl amine | 0.0001 | 0.001 | 0.005 | 0.02 | 0.07 | 0.2 | 3 |
| acetaldehyde | 0.002 | 0.01 | 0.05 | 0.1 | 0.5 | 1 | $1 * 10$ |
| propionaldehyde | 0.002 | 0.02 | 0.05 | 0.1 | 0.5 | 1 | 10 |
| n-butylaldehyde | 0.0003 | 0.003 | 0.009 | 0.03 | 0.08 | 0.3 | 2 |
| i-butylaldehyde | 0.0009 | 0.008 | 0.02 | 0.07 | 0.2 | 0.6 | 5 |
| n-valeraldehyde | 0.0007 | 0.004 | 0.009 | 0.02 | 0.05 | 0.1 | 0.6 |
| i-valeraldehyde | 0.0002 | 0.001 | 0.003 | 0.006 | 0.01 | 0.03 | 0.2 |
| i-butanol | 0.01 | 0.2 | 0.9 | 4 | 20 | 70 | $1 * 10^3$ |
| ethyl acetate | 0.3 | 1 | 3 | 7 | 20 | 40 | $2 * 10^2$ |
| methylisobutyrketone | 0.2 | 0.7 | 1 | 3 | 6 | 10 | 50 |
| toluene | 0.9 | 5 | 10 | 30 | 60 | $1 * 10^2$ | $7 * 10^2$ |
| styrene | 0.03 | 0.2 | 0.4 | 0.8 | 2 | 4 | $2 * 10$ |
| xylene | 0.1 | 0.5 | 1 | 2 | 5 | 10 | 50 |
| propionic acid | 0.002 | 0.01 | 0.03 | 0.07 | 0.2 | 0.4 | 2 |
| n-acetic acid | 0.00007 | 0.0004 | 0.001 | 0.002 | 0.006 | 0.02 | 0.09 |
| n-valeric acid | 0.0001 | 0.0005 | 0.0009 | 0.002 | 0.004 | 0.008 | 0.04 |
| i-valeric acid | 0.00005 | 0.00004 | 0.001 | 0.004 | 0.01 | 0.03 | 0.3 |

Although the automobile air conditioner was described as an example, the present invention is applicable to any situation where an air-cooling system is used in a confined space, including in a home or workplace.

The method for detecting and analyzing materials contributing to an odor emitted from an air conditioner according to the present invention may be used to analyze offensive odor emitted from an air conditioner and develop an apparatus or a method for removing the specific odor.

The present invention has been described in detail with reference to exemplary embodiments thereof. However, it will be appreciated by those skilled in the art that various changes and modifications may be made in these embodiments without departing from the principles and spirit of the invention, the scope of which is defined in the appended claims and their equivalents.

What is claimed is:

1. A method for detecting and analyzing materials contributing to a detected odor from an air conditioner, the method comprising:
analyzing the detected odor using a sensory evaluation;
collecting a first gas sample emitted from an automobile air conditioner for instrumental analysis;
analyzing the first gas sample using instrumental analysis;

reproducing a plurality of contributing materials of the detected odor; and enhancing odor intensity by increasing the concentration of the determined contributing materials by one level, wherein the level is based on the odor intensity indication which is obtained through the sensory evaluation and the instrumental analysis.

2. The method according to claim 1, wherein reproducing a plurality of contributing materials of the detected odor further comprises:

determining a plurality of representative offensive odor causing materials;

combining the plurality of representative offensive odor causing materials to reproduce the detected odor; and adding a plurality of volatile organic compounds (VOCs) when the detected odor is not reproduced by the plurality of representative offensive odor causing materials.

3. The method according to claim 1, wherein reproducing a plurality of contributing materials of the detected odor further comprises:

conducting an instrumental analysis on second gas sample separately collected in sections where the quality and intensity of odor change using the following pattern analysis steps, and figuring out elements of the odor based on the results of the analysis, wherein the second gas sample is discharged through an automobile air-conditioner, wherein sections where the quality and intensity of odor change mean the sections where a peak values increase, wherein the peak values are the result of the sensory evaluation by a panel of individuals when the automobile air conditioner is turned on/off, wherein the pattern analysis steps are the following gas analysis equations pattern analysis step 1: [A/C off−indoor air]>0;

pattern analysis step 2: [A/C off−A/C on]>0; and pattern analysis step 3: [(A/C off−indoor air) and (A/C off−A/C on)]>0;

wherein the second gas sample is collected when any one of the pattern analysis steps 1 to 3 is satisfied, wherein a gas collection using pattern analysis step 1 is made when a difference of an instrumental analysis value by the panel of individuals between indoor air and A/C off is more than 0, and the gas is collected when indoor air is changed to 'A/C off,' wherein the 'A/C off' means when a blower is turned on, a surface of evaporator core is in a dry state, and 'indoor air' means inside air of a general automobile when the blower is turned off, wherein a gas collection using pattern analysis step 2 is made when a difference of an instrumental analysis value by the panel individuals between 'A/C off' and 'A/C on' is more than 0, wherein 'A/C on' is when the blower is turned on, the air conditioner is under an internal ventilation condition, a surface of the evaporator core is in a wet state, and 'A/C off' is when the blower is turned on and a surface of the evaporator core is in a wet state, and wherein a gas collection using pattern analysis step 3 is made when both of pattern analysis steps 1 and 2 are satisfied.

* * * * *